United States Patent [19]

Maruoka

[11] 4,212,273
[45] Jul. 15, 1980

[54] AIR FUEL SUPPLY SYSTEM AND OXYGEN SENSOR THEREFOR

[76] Inventor: Hiroyuki Maruoka, No. 3-4-5, Kami-ohokanishi, Konan-ku, Yokohama City, Japan

[21] Appl. No.: 840,244

[22] Filed: Oct. 7, 1977

[30] Foreign Application Priority Data

Oct. 8, 1976 [JP] Japan .................. 51-121406

[51] Int. Cl.² .............. G01N 27/58; F02M 7/00
[52] U.S. Cl. .................. 123/438; 204/195 S; 123/549
[58] Field of Search .......... 204/195 S, 1 S; 60/276; 123/119 E, 119 EC; 324/29; 422/98

[56] References Cited

U.S. PATENT DOCUMENTS 4,132,615  1/1979  Linder et al. ................ 204/195 S

FOREIGN PATENT DOCUMENTS 2416629  10/1975  Fed. Rep. of Germany ....... 204/195 S Primary Examiner—G. L. Kaplan
Attorney, Agent, or Firm—Schwartz, Jeffery, Schwaab, Mack, Blumenthal & Koch

[57] ABSTRACT

A concentration cell comprising an electrolyte with two surfaces respectively covered with two metallic electrodes is partially mantled by a layer of an oxidizing catalyst. Heating means is disposed in the catalyst for heating it when electrically energized.

13 Claims, 3 Drawing Figures

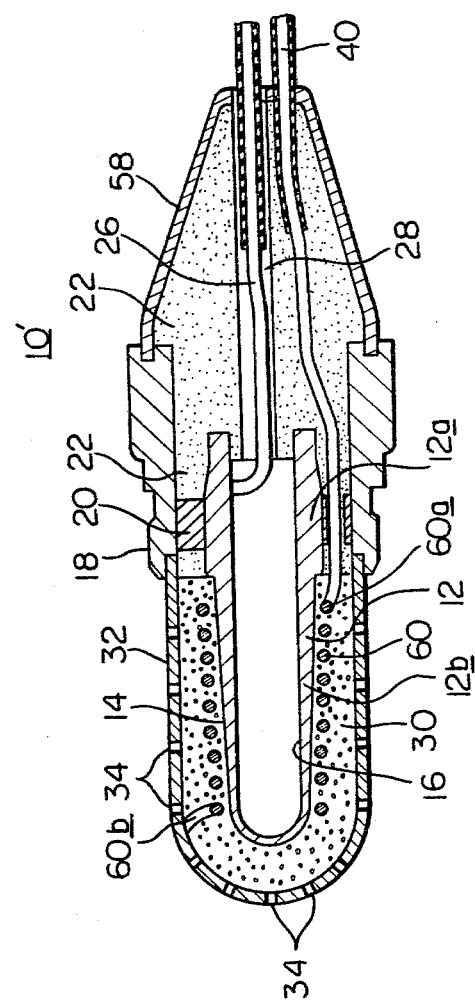

AIR FUEL SUPPLY SYSTEM AND OXYGEN SENSOR THEREFOR

FIELD OF THE INVENTION

The present invention relates in general to a gas sensor and more particularly to an electro-chemical sensing device to sense the air-fuel ratio of an air-fuel mixture fed into an internal combustion engine by determining the oxygen content in the mixture.

BACKGROUND OF THE INVENTION

For controlling the air-fuel ratio of the air-fuel mixture at the stoichiometric ratio, a so-called closed loop control system having an oxygen sensor placed in communication with the exhaust gases issued from the engine has been widely used. The oxygen sensor generates an electrical signal responsive to the oxygen content of the exhaust gases. The electrical signal, in turn, is applied to a control means connected to the engine for regulating or varying the character of the air-fuel mixture so as to maintain the same at the stoichiometric ratio.

With the above-stated conventional system, however, there inevitably arises a drawback in which the variation of the air-fuel ratio of the intake charge prepared by the carburetor or the like is determined by the sensor placed in the exhaust conduit considerably after the combustion of the corresponding intake charge, thereby causing the control system to have a relatively long responses time. This means that an effective control can not be expected in the above-mentioned type control system.

Therefore, the present invention contemplates to eliminate the drawback encountered in the conventional closed loop control system.

An object of the present invention is to provide a new and improved oxygen sensor with which a closed loop air-fuel mixture supply control system can afford a quick response.

Another object of the invention is to provide a new and improved oxygen sensor which is designed to mount in an intake conduit system of the internal combustion engine.

Still another object of the present invention is to provide a new and improved oxygen sensor which is compact in size.

According to the present invention, there is provided a gas sensor comprising a casing, a solid electrolyte disposed in the casing and having first and second surfaces which are respectively covered with first and second metallic electrodes, the first metallic electrode being adapted to be exposed to a gas subject to measurement and the second metallic electrode being adapted to be exposed to a reference gas; supporting means supporting the electrolyte in the casing; a layer of oxidizing catalyst disposed on the first metallic electrode to cover the same; an electric heat generator separate and distinct from said catalyst and disposed in said layer of the catalyst for generating heat when electrically energized; and lead wires operatively connected to said electric heat generator for transmitting electric current to said generator.

BRIEF DESCRIPTION OF THE DRAWINGS

Other objects and advantages of the present invention will become apparent from the following detailed description when taken in conjunction with the accompanying drawings, in which:

FIG. 3 is a view similar to FIG. 1, but showing a second embodiment of the present invention.

DESCRIPTION OF THE PREFERRED EMBODIMENTS

Figure 1:
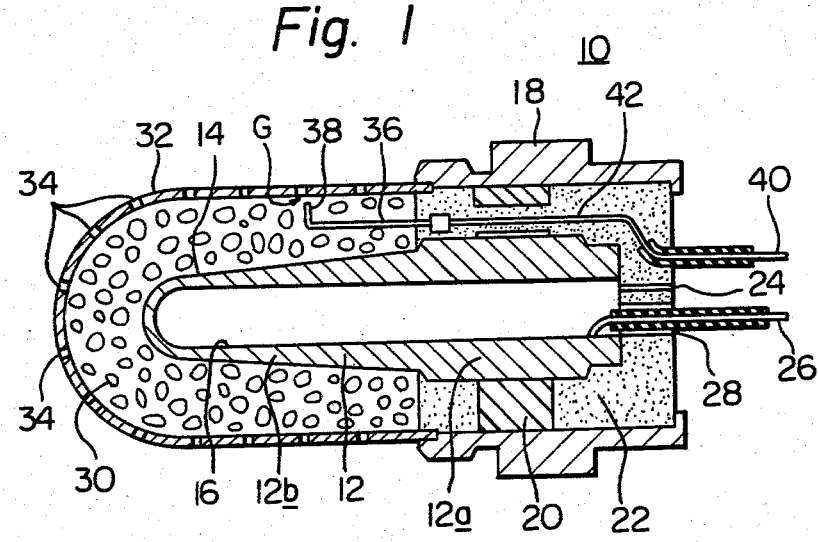
FIG. 1 is a sectional view of a first embodiment of an oxygen sensor of the present invention.

Referring to FIG. 1 of the drawings, there is illustrated a new and improved oxygen sensor of the invention, as being generally designated by numeral 10. The sensor 10 comprises a solid electrolyte tube 12, which is closed at one end and open at the other end. As shown, the tube 12 has a collar section 12a adjacent its open end and a conical section 12b that tapers to its thinnest closed end from the collar section 12a. The tube 12 may, for example, be made of stabilized zirconium dioxide ($ZrO_2$). The outer and inner surfaces of the tube 12 are respectively covered or coated with first and second platinum layers 14 and 16 which act as first and second electrodes. The solid electrolyte tube 12 is secured in a suitably shaped socket or base member 18 made of metal by disposing a conductive ring member 20 and an insulating material 22 between the collar section 12a and the socket 18. The ring member provides an electrical connection between the first electrode 14 and the socket 18. The insulating material 22 covers the open end of the electrolyte 12 and has a passage 24 providing a fluid communication between the interior of the tube 12 and the open air. A lead wire 26 is passed through another passage 28 formed in the insulating material 22 to connect with the second electrode 16. Of course, the passage 24 may be omitted so long as the passage 28 is formed to allow a sufficient fluid communication between the interior of the tube 12 and the open air. With this, a so-called concentration cell is formed.

According to the present invention, the following measure is further required. As shown, the conical section 12b of the solid electrolyte tube 12 is surrounded by a layer of oxidizing catalyst 30 which is tightly held or supported by a porous tubular metal cover 32 fixed at its one end to the socket 18. Designated by numerals 34 are openings of the cover 32. An elongate spark electrode 36 is stationarily disposed in the catalyst 30 with one bent end 38 thereof located to provide a suitable gap "G" between it and the cover 32. The other end of the spark electrode 36 is connected to a lead wire 40 which passes through the insulating material 22 and through a passage 42 formed in the ring member 20. If desired, the spark electrode 36 may be formed to have its integral extension which is projected to the open air passing through the insulating material 22.

Figure 2:
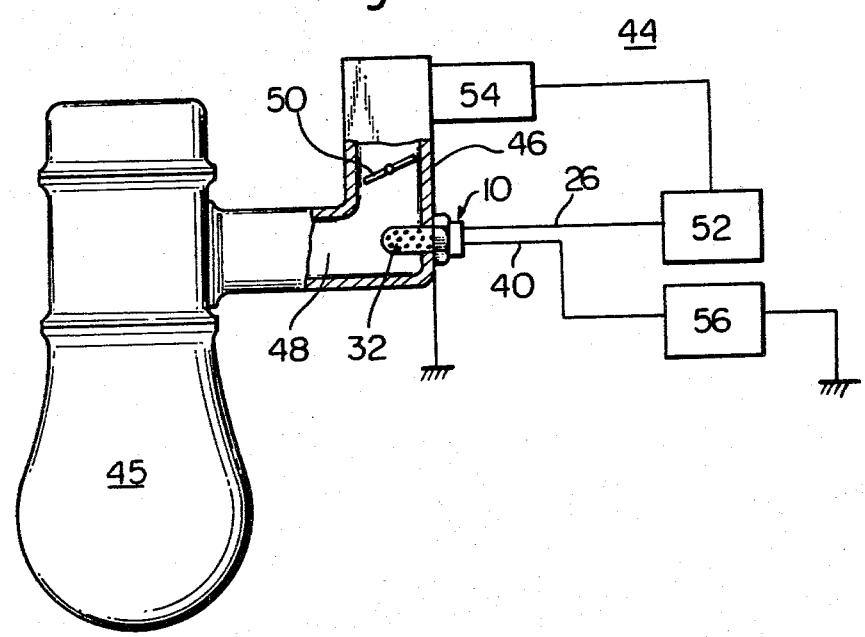
FIG. 2 is a schematic view of a closed loop air-fuel mixture supply control system in which an oxygen sensor of the invention is mounted in the intake conduit of the internal combustion engine.

Referring to FIG. 2, there is shown an arrangement in which the above-mentioned oxygen sensor 10 cooperates with a closed loop air-fuel mixture supply control system 44 of an internal combustion engine 45. The control system 44 hereinshown essentially includes the oxygen sensor 10 which is mounted on an intake conduit 46 so as to project at its metal cover 32 into an intake passage 48 downstream of a throttle valve 50. With this, the socket 18 of the sensor 10 is grounded through the intake conduit 46. The lead wire 26 connected to the second electrode 16 of the sensor 10 leads to a control unit 52 which in turn connects to an electronically controlled air-fuel mixture supply means 54. The means 54 may be either of a type to directly control the amount of fuel fed into intake passage 48 or of a type to control the amount of fuel by varying the open area of the bleeding passage thereof in response to command signals applied thereto. The lead wire 40 connected to the spark electrode 36 leads to a high tension electric power source 56. The power source 56 may be a conventional ignition circuit comprising a D. C. battery, an ignition coil and a distributor.

With this arrangement including the oxygen sensor 10, the operation of the control system 44 is as follows:

When an ignition switch (not shown) is closed to start the engine 45, the electric power source 56 produces intermittently the high tension voltage which jumps across the gap "G" defined between the bent end 38 of the spark electrode 36 and the metal cover 32, creating a spark. The heat of this spark makes the oxidation catalyst 30 warm and simultaneously ignites the fuel which has been penetrated into the catalyst 30 through the openings 34 of the cover 32. By this, not only the oxidation catalyst 30 but also the concentration cell consisting of the electrolyte 12 with the first and second electrodes 14 and 16 are quickly warmed up to quickly achieve their top effeciencies. The concentration cell senses the oxygen content contained in the combusted gases produced in the layer of the catalyst 30 to apply to the control unit 52 an information signal representing the air-fuel ratio of the air-fuel mixture being fed to the engine 45. Upon receiving the information signal, the control unit 52 issues a command signal to the air-fuel mixture supply means 54 to cause the same to supply the engine 45 with intake mixture having a desired or stoichiometric air-fuel ratio. It should be noted that once the catalyst 30 operates, the operation continues by the heat of reaction to maintain the desired temperature of the catalyst 30, inducing effective reaction effeciency. Furthermore, since the sensor 10 is exposed to the air-fuel mixture having a relatively low temperature, the sensor 10 is prevented from being overly heated.

In addition to the above-stated construction, it may be possible to provide the control system 44 with a timer means (not shown) which blocks the electrical connection between the spark electrode 36 and the power source 56 to stop the spark when the heating by the spark exceeds beyond a predetermined time, and/or a temperature sensing means (not shown) which blocks the connection when the temperature of the oxygen sensor 10 exceeds a predetermined degree.

Referring to FIG. 3, a modified form of the oxygen sensor according to the invention is illustrated, as being generally designated by numeral 10'. For simplification, similar parts to the before-mentioned first embodiment of FIG. 1 will be designated by the same numerals. Designated by numeral 58 in the drawing is a conical cover for the insulating material 22. In this modified case 10', a wire heater 60 having multiple turns, forming a coil, spacedly disposed around the conical section 12b of the electrolyte 12 is used as a substitute for the spark electrode 36 of FIG. 1. One end 60a of the heater 60 is connected to the lead wire 40 and the other end 60b thereof is connected to the metal cover 32 as shown.

When the sensor 10' is arranged in a closed loop air-fuel mixture supply system such as one shown in FIG. 2, the lead wire 40 from the wire heater 60 is connected to a conventional electric power source such as a D. C. battery. Of course in this case, the before-mentioned timer means and the temperature sensing means may be equipped in the control system.

From the above, it will be appreciated that the sensor 10 or 10' embodying the present invention can exhibit its effective function quickly even when arranged in an intake conduit thereby allowing the closed loop air-fuel mixture supply control system including such sensor to optimally operate.

It should be noted that the foregoing description shows only two exemplary embodiments. Various modifications and improvements are apparent to those skilled in the art without departing from the scope of the present invention which is only defined by the appended claims.

What is claimed is:

1. A gas sensor comprising:
    a casing;
    a solid electrolyte disposed in said casing and having first and second surfaces which are respectively covered with first and second metallic electrodes, said first metallic electrode being adapted to be exposed to a gas subject to measurement and said second metallic electrode being adapted to be exposed to a reference gas;
    supporting means supporting said electrolyte in said casing;
    a layer of oxidizing catalyst disposed on said first metallic electrode to cover at least a portion of same; and
    an electric heat generator separate and distinct from said catalyst and disposed in said layer of the catalyst for generating heat when electrically energized.

2. A gas sensor as claimed in claim 1, in which said heat generator comprises:
    a porous metallic cover covering said layer of oxidizing catalyst; and
    a spark electrode disposed in said catalyst with an end thereof positioned adjacent a portion of said metallic cover to form a spark gap between said end and said portion,
    said spark gap being sized to create a spark therein when a predetermined high tension voltage is applied between said metallic cover and said spark electrode.

3. A gas sensor as claimed in claim 1 in which said heat generator comprises a heat wire disposed in said catalyst.

4. A gas sensor as claimed in claim 3, in which said wire has multiple turns, forming a coil, spacedly disposed around said electrolyte.

5. A gas sensor as claimed in claim 4, further comprising a porous metallic cover covering said layer of oxidizing catalyst and having a portion to which an end of said wire is connected.

6. A gas sensor as claimed in claim 1, in which said supporting means includes a conductive ring providing an electrical connection between said first metallic electrode and said casing.

7. A gas sensor as claimed in claim 6, in which said supporting means further includes an insulating material disposed in a space defined between said casing and said electrolyte.

8. An oxygen sensor for determining oxygen content in a gas mixture, comprising:
    a tubular casing made of metal;
    a tubular solid electrolyte having a closed end and an open end and spacedly disposed in said casing;

first and second metallic electrodes respectively covering exterior and interior surfaces of said electrolyte while being electrically insulated from each other; said first metallic electrode being adapted to be exposed to said gas mixture to be measured and said second metallic electrode being adapted to be exposed to a reference gas;

a conductive ring member coaxially disposed in an annular space defined between said casing and said electrolyte to provide an electrical connection between said casing and said first metallic electrode;

a layer of oxidizing catalyst disposed on said first metallic electrode so as to cover a portion of said first metallic electrode, said portion including said closed end of said electrolyte;

an insulating material disposed in said annular space with said ring member;

a porous metallic cover covering said layer of oxidizing catalyst and fixed to said casing; and an electric heat generator separate and distinct from said catalyst and disposed in said layer of the catalyst for generating heat when electrically energized.

9. An oxygen sensor as claimed in claim 8, in which said heat generator comprises a spark electrode disposed in said catalyst, said spark electrode having an end bent toward a portion of said porous metallic cover to define a spark gap between said end and said cover portion, said spark gap being sized to create a spark therein when a predetermined high voltage is applied between said metallic cover and said spark electrode.

10. An oxygen sensor as claimed in claim 8, in which said heat generator comprises a wire which has multiple turns spacedly disposed around a portion of said first electrode, said coil having one end connected to said metal cover and another end adapted for connection to a voltage source.

11. An air-fuel mixture supply system for an internal combustion engine having an intake conduit system in which a throttle valve is operatively arranged, comprising:

an air-fuel mixture supply means for controlling the amount of fuel fed into the engine in response to command signals applied thereto;

a control unit for applying said command signals to said air-fuel mixture supply means in response to information signals applied thereto;

an oxygen sensor disposed in said intake conduit system to project into an intake passage downstream of said throttle valve, said sensor producing said information signals by detecting the oxygen content in said intake passage and comprising a casing electrically and mechanically connected to said intake conduit system, an electrolyte disposed in said casing and having first and second surfaces which are respectively covered with first and second metallic electrodes, said first metallic electrode being adapted to be exposed to the interior of said intake passage and second metallic electrode being adapted to be exposed to a reference gas, an electrically conductive supporting member disposed in said casing to support said electrolyte while providing an electrical connection between said first metallic electrode and said casing, a layer of oxidizing catalyst disposed in said first metallic electrode to mantle said electrolyte while being exposed to the interior of said intake passage, and an electric heat generator separate and distinct from said catalyst and disposed in said layer of catalyst for generating heat when electrically energized; and an electrical power source for energizing said heating means within a predetermined period of time after starting of said engine.

12. A gas sensor for sensing the air-fuel ratio of the air-fuel mixture in the intake conduit of an internal combustion engine comprising:

a casing adapted for mounting in said intake conduit;

a solid electrolyte disposed in said casing and having first and second surfaces which are respectively covered with first and second metallic electrodes, said first metallic electrode being adapted to be exposed to a gas subject to measurement in said intake conduit and said second metallic electrode being adapted to be exposed to a reference gas;

supporting means for supporting said electrolyte in said casing;

a layer of oxidizing catalyst disposed on said first metallic electrode to cover at least a portion of same;

an electric heat generator separate and distinct from said catalyst and disposed in said layer of the catalyst for generating heat when electrically energized; and lead wires operatively connected to said electric heat generator for transmitting electric current to said generator.

13. An oxygen sensor for sensing the air-fuel ratio of the air-fuel mixture in the intake conduit of an internal combustion engine, comprising:

a tubular casing made of a metal and adapted for mounting in said intake conduit;

a tubular solid electrolyte having a closed end and an open end and spacedly disposed in said casing;

a first and second metallic electrodes respectively covering exterior and interior surfaces of said electrolyte while being electrically insulated from each other, said first metallic electrode being adapted to be exposed to a gas to be measured in said intake conduit and said second metallic electrode being adapted to be exposed to a reference gas;

a conductive ring member coaxially disposed in an annular space defined between said casing and said solid electrolyte to provide an electrical connection between said casing and said first metallic electrode;

a layer of oxidizing catalyst disposed on said first metallic electrode so as to cover a portion of said electrolyte, said portion including said closed end;

an insulating material disposed in said annular space with said ring member;

a porous metallic cover covering said layer of oxidizing catalyst and fixed to said casing;

an electric heat generator separate and distinct from said catalyst and disposed in said layer of oxidizing catalyst for heating said catalyst when electrically energized; and lead wires operatively connected to said electric heat generator for transmitting electric current to said generator.

* * * * *